United States Patent
Eller et al.

(10) Patent No.: US 11,379,794 B2
(45) Date of Patent: *Jul. 5, 2022

(54) METHODS AND SYSTEMS FOR FULFILLING DRUG ORDERS

(71) Applicant: Express Scripts Strategic Development, Inc., St. Louis, MO (US)

(72) Inventors: Charles E. Eller, Lake Saint Louis, MO (US); Jonathan W. Joplin, Chesterfield, MO (US)

(73) Assignee: Express Scripts Strategic Development, Inc., St. Louis, MO (US)

( * ) Notice: Subject to any disclaimer, the term of this patent is extended or adjusted under 35 U.S.C. 154(b) by 536 days.

This patent is subject to a terminal disclaimer.

(21) Appl. No.: 16/418,952

(22) Filed: May 21, 2019

(65) Prior Publication Data

US 2019/0272609 A1   Sep. 5, 2019

Related U.S. Application Data

(63) Continuation of application No. 13/340,318, filed on Dec. 29, 2011, now Pat. No. 10,325,333.

(51) Int. Cl.
| | | |
|---|---|---|
| *G16H 20/13* | (2018.01) | |
| *G06Q 10/10* | (2012.01) | |
| *G16H 40/67* | (2018.01) | |
| *G16H 20/10* | (2018.01) | |

(52) U.S. Cl.
CPC .............. *G06Q 10/10* (2013.01); *G16H 20/10* (2018.01); *G16H 20/13* (2018.01); *G16H 40/67* (2018.01)

(58) Field of Classification Search
CPC ..................................................... G06Q 10/10
See application file for complete search history.

(56) References Cited

U.S. PATENT DOCUMENTS

| | | | | |
|---|---|---|---|---|
| 4,847,764 A | * | 7/1989 | Halvorson | ........... G06Q 10/087 700/231 |
| 5,845,255 A | | 12/1998 | Mayaud | |

(Continued)

FOREIGN PATENT DOCUMENTS

WO   199829823   7/1998

*Primary Examiner* — Robert A Sorey
(74) *Attorney, Agent, or Firm* — Miller Johnson (57) ABSTRACT

A drug dispensing system includes fulfillment stations that are each characterized by a set of dispensary attributes. The fulfillment stations each, in response to receiving a first order message including a first unique drug identifier, fill a container with pills matching the first unique drug identifier. A routing determination module, for each order message corresponding to a prescription order, selects one of the fulfillment stations based on compatibility between dispensary attributes for the selected fulfillment station and dispensation preferences related to the order message and transmits the order message to the selected fulfillment station. An order status subsystem conditionally sends a cancellation instruction relating to one of the order messages to the respective fulfillment station to cancel dispensing of pills. Each fulfillment station is configured to, in response to receiving a first cancellation instruction indicating a specified order message, terminate dispensing of pills corresponding to the specified order message.

20 Claims, 7 Drawing Sheets

(56) References Cited

U.S. PATENT DOCUMENTS

| | | | |
|---|---|---|---|
| 6,021,392 A * | 2/2000 | Lester | G16H 70/40 |
| | | | 705/2 |
| 6,529,801 B1 | 3/2003 | Rosenblum | |
| 7,337,129 B1 | 2/2008 | Lowry et al. | |
| 7,574,370 B2 | 8/2009 | Mayaud | |
| 8,060,248 B1 * | 11/2011 | Boyer | B65B 57/20 |
| | | | 700/235 |
| 2002/0128919 A1 | 9/2002 | Rime et al. | |
| 2003/0050731 A1 | 3/2003 | Rosenblum | |
| 2004/0088187 A1 | 5/2004 | Chudy | |
| 2004/0108323 A1 | 6/2004 | Shows et al. | |
| 2004/0122713 A1 | 6/2004 | Hill | |
| 2005/0049746 A1 | 3/2005 | Rosenblum | |
| 2005/0144053 A1 | 6/2005 | Mauthe et al. | |
| 2006/0116905 A1 | 6/2006 | Yered | |
| 2006/0259322 A1 | 11/2006 | Chin et al. | |
| 2006/0265245 A1 | 11/2006 | McCallie et al. | |
| 2007/0112602 A1 | 5/2007 | Bellon et al. | |
| 2007/0136376 A1 | 6/2007 | Kusakabe | |
| 2009/0287350 A1 * | 11/2009 | Johnson | G07F 9/0235 |
| | | | 700/236 |
| 2010/0070298 A1 | 3/2010 | Kalies | |
| 2010/0125461 A1 | 5/2010 | Heald et al. | |
| 2010/0168904 A1 * | 7/2010 | Henderson | G16H 20/13 |
| | | | 700/216 |
| 2011/0251850 A1 | 10/2011 | Stephens | |
| 2012/0253829 A1 * | 10/2012 | John | G16H 40/67 |
| | | | 705/2 |

* cited by examiner

METHODS AND SYSTEMS FOR FULFILLING DRUG ORDERS

CROSS-REFERENCE TO RELATED APPLICATIONS

This application is a continuation of U.S. patent application Ser. No. 13/340,318 filed Dec. 29, 2011. The entire disclosure of the application referenced above is incorporated by reference.

FIELD

This disclosure relates to fulfilling prescription orders, and more particularly to the use of a fulfillment gateway to identify a location for fulfillment of a prescription and/or prescription drug delivery.

BACKGROUND

At a data entry location for fulfillment of prescription drugs, the name of a patient of a pharmacy, the name of the prescribed drug(s), strength of the drug(s), prescriber identification, and directions for administering the drug(s) are entered. Prescription drugs are increasingly filled at a location separate from the data entry location. That is, upon verification of a valid prescription, the prescription is fulfilled at a fulfillment location remote from the data entry location.

The fulfillment location often needs additional information from the data entry location in order to fulfill the prescription accurately. During fulfillment of some prescriptions at the fulfillment location, the prescription, and therefore the fulfillment, must be altered. Should the prescription be fulfilled without being altered, the prescription is likely unusable at considerable expense. Because of the possibility of a prescription being altered during fulfillment, the fulfillment location sends frequent requests for updates on the prescription to the data entry location at various stages of fulfillment. The requests for updates attempt to catch any alterations to the prescription that would then, accordingly, require alterations to the fulfillment. These requests for updates from multiple locations can be numerous and burdensome for the data entry location. Furthermore, if the data entry location loses communication with the fulfillment location, the fulfillment of the prescription may be put on hold indefinitely because no updates are received. The loss of communication may cause a large number of such holds and a corresponding loss in operating income.

In other operations, the fulfillment location only receives information about the prescription from the data entry location in parts or stages. To properly complete fulfillment, the fulfillment location then has to request more information about the prescription. Likewise, if the data entry location loses contact with the fulfillment location, the fulfillment of numerous prescriptions can come to a standstill. In other situations, the fulfillment location is selected at the data entry location. The data entry location may select a fulfillment location based on location of patient (e.g. zip code) to minimize shipping costs. However, there may be backlogs, low inventory or significant price increases, for example, of which the data entry location is unaware. Once a fulfillment location is selected, fulfillment of the prescription is committed to the chosen fulfillment location.

DETAILED DESCRIPTION

Example methods and systems for fulfilling prescription orders are described. In the following description, for purposes of explanation, numerous specific details are set forth in order to provide a thorough understanding of example embodiments. It will be evident, however, to one of ordinary skill in the art that embodiments of the invention may be practiced without these specific details.

Generally, an order processing station provides processing of a prescription to develop a prescription order for sending to an order fulfillment station via a fulfillment gateway. Examples of some of the operations of the fulfillment gateway and its interactions with order processing stations and order fulfillment stations are described below.

When the prescription order arrives at the fulfillment gateway from the order processing station, an order fulfillment station has not been selected. The fulfillment gateway associates the prescription order with an order message and provides information needed for an order fulfillment station to fulfill the prescription according to the prescription order.

The fulfillment gateway selects the order fulfillment station based on prescription parameters, dispensation preferences and dispensary attributes. Rules and/or priorities for treatment of various prescription parameters, dispensation preferences and dispensary attributes may govern selection of an order fulfillment station. The fulfillment gateway described herein is generally sensitive to cost of labor, material, and shipping involved with fulfillment of a prescription according to a prescription order.

The fulfillment gateway holds completed prescription orders associated with order messages for the order fulfillment station to pull or download from the fulfillment gateway as needed. Furthermore, the fulfillment gateway tracks progress of fulfillment at order fulfillment stations. Thus, the order fulfillment station does not have to request updates from the order processing station. Indeed, the order fulfillment station does not need to communicate with the order processing station. That is, the order fulfillment station is independent or decoupled from the order processing station. Thus, irrespective of the status of the order processing station, the fulfillment gateway allows routing and fulfillment to continue. The fulfillment gateway allows delay of a routing decision so that an order fulfillment station does not need to be selected at the order processing station. The fulfillment gateway provides capabilities for changing routing of the prescription order. That is, by tracking progress, the fulfillment gateway may stop, pause, cancel or change prescription orders during fulfillment of the prescription.

Figure 1:
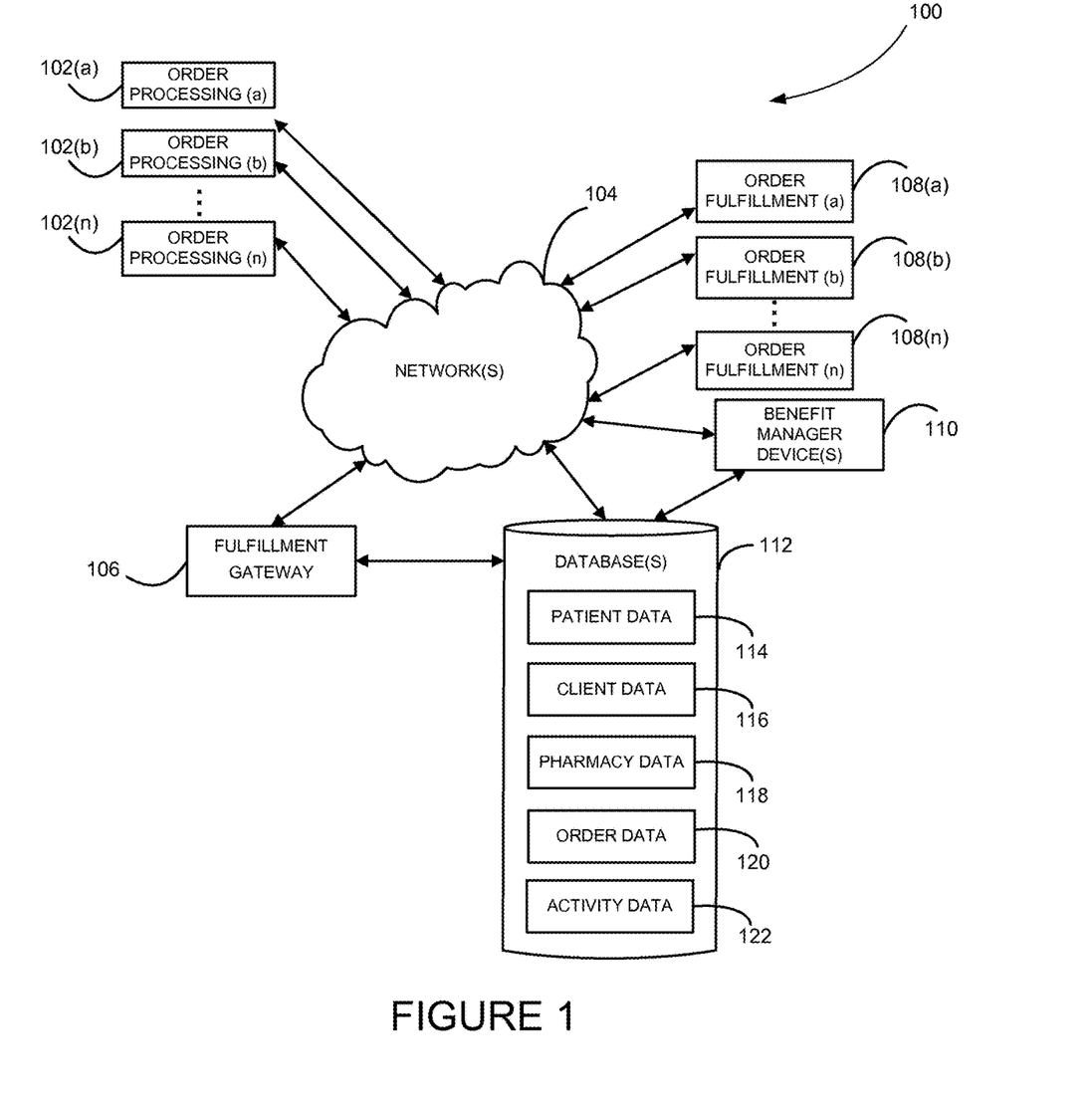
FIG. 1 is a block diagram of an example system, according to an example embodiment.

FIG. 1 is a block diagram of an example system 100, according to an example embodiment. The system 100 is an example environment in which a prescription may be fulfilled. The system 100 as shown in FIG. 1 includes multiple order processing stations 102(a)-(n) and multiple order fulfillment stations 108(a)-(n) that are in communication with a fulfillment gateway 106 over a network 104. The system 100 may further include one or more benefit manager devices 110. The benefit manager device 110 is in communication with the order processing station 102 over the network 104 and assists in processing of a prescription to develop a prescription order for sending to an order fulfillment station 108 via the fulfillment gateway 106.

The order processing station 102 is a device or system operated by an entity that is at least partially responsible for data entry and verification of prescriptions. The order processing station 102 may be in communication with a benefits manager device 110 to adjudicate pharmacy insurance claims associated with the prescription, for example. The order processing station 102 may communicate with the benefits manager device 110 to verify inclusion of a prescription drug in a formulary and obtain suggestions for substitutions of the prescription drug not in the formulary. The order processing station 102 verifies the eligibility of the patient, i.e., substantiates that the patient is a member of a drug benefit plan or a beneficiary of the member (e.g., a spouse or a child of the beneficiary). The order processing station 102 may also verify that the prescription from the prescriber meets pharmacy policies and local, state and federal regulations. Verification of the prescription may entail the authentication of prescription parameters, such as name of prescription drug, identification of patient, strength of the prescription drug, quantity of the prescription drug, identification of prescriber and directions for administering the prescription drug.

The network 104 may include, by way of example, Mobile Communications (GSM) network, a code division multiple access (CDMA) network, 3rd Generation Partnership Project (3GPP), an Internet Protocol (IP) network, a Wireless Application Protocol (WAP) network, a WiFi network, or an IEEE 802.11 standards network, as well as various combinations thereof. Network 104 may also include optical communications. Other conventional and/or later developed wired and wireless networks may also be used.

Moreover, system 100 shows a single network 104; however, multiple networks can be used. The multiple networks may communicate in series with each other to link the devices 102, 106, 108, 110, 112 or in parallel to link the devices 102, 106, 108, 110, 112. For example, the network between the fulfilment gateway 106 and the order processing stations 102 may be separate from the network between the fulfilment gateway 106 and the order fulfillment stations 108.

An order fulfillment station 108 may be a mail order pharmacy, a retail pharmacy, a specialty pharmacy or other types of pharmacies. Each of the order fulfillment stations 108 may have the same or different capabilities at various locations. Some order fulfillment stations 108 may specialize in fulfilling prescriptions for expensive drugs, such as cancer drugs, while some order fulfillment stations 108 may specialize in high-speed fulfillment of high-volume prescription drugs. Some order fulfillment stations 108 may be strategically located at, for example, large metro areas for proximity to a large number of patients while others are located away from large metro areas to reduce operational costs. The order fulfillment stations 108 may have a large inventory of prescription drugs from which to pull when needed for fulfillment of prescriptions. Other order fulfillment stations 108 may limit inventory by ordering prescription drugs from distributors for strategically timed delivery to avoid inventory costs. The order fulfillment stations 108 may have other capabilities such as marking caps or vials, specialty packaging, cold rooms, added security for class C-2 narcotic prescription drugs, and the like.

The benefit manager device 110 is a device operated by an entity at least partially responsible for creation and/or management of the pharmacy benefit. While the benefit manager operating the benefit manager device 110 is typically a PBM, other entities may operate the benefit manager device 110 either on behalf of themselves, the PBM, or another entity.

Some of the operations of the PBM that operates the benefit manager device 110 may include the following. A member (or a person on behalf of the member) attempts to obtain a prescription drug at a retail pharmacy location where the member can obtain drugs in a physical store from a pharmacist or pharmacist technician, or in some instances through mail order drug delivery from a mail order pharmacy location.

The member may have a co-pay for the prescription drug that reflects an amount of money that the member is responsible to pay the pharmacy for the prescription drug. The money paid by the member to the pharmacy may come from the personal funds of the member, a health savings account (HSA) of the member or the member's family, a health reimbursement arrangement (HRA) of the member or the member's family, a flexible spending accounts (FSA) of the member or the member's family, or the like. An employer of the member may directly or indirectly fund or reimburse the member or an account of the member for the co-pay.

The amount of the co-pay paid by the member may vary by the benefit plan of the client with the PBM. The member's co-pay may be based on be a flat co-pay (e.g., $10), co-insurance (e.g., 10%), and/or a deductible (e.g., for first $500 of annual prescription drug spend) for certain prescription drugs, certain types of prescription drugs, and/or all prescription drugs.

In certain instances, the member may not pay the co-pay or may only pay for a portion of a co-pay for a prescription drug. For example, if the usual and customary cost for a generic version of a prescription drug is $4, and the member's flat co-pay is $20 for the prescription drug, the member may only pay $4 to receive the prescription drug. In another example involving a worker's compensation claim, no co-pay may be due by the member for the prescription drug.

In conjunction with receiving the co-pay (if any) from the member and dispensing the prescription drug to the member, the pharmacy submits a claim to the PBM for the prescription drug. The PBM may perform certain adjudication functions including verifying the eligibility of the member, reviewing the formulary to determine appropriate co-pay, coinsurance, and deductible for the prescription drug, and performing a drug utilization review (DUR) on the member. The PBM then adjudicates the claim associated with the prescription drug and provides a response to the pharmacy following performance of the aforementioned functions. As part of the adjudication, the client (or the PBM on behalf of the client) ultimately reimburses the pharmacy for filling the prescription drug when the prescription drug was successfully adjudicated. The aforementioned adjudication functions generally occur before the co-pay is received and the prescription drug dispensed. However, the operations may occur simultaneously, substantially simultaneously, or in a different order. In addition, more or less adjudication functions may be performed as part of the adjudication process.

The amount of reimbursement paid to the pharmacy by the client and/or member may be based at least in part on the type of pharmacy network in which the pharmacy is included. Other factors may be used to determine the reimbursement amount in addition to the type of pharmacy network.

The order processing stations 102 may be geographically separated from the order fulfillment stations 108 and the fulfillment gateway 106. The order processing stations 102, the order fulfillment stations 108, and/or the fulfillment gateway 106 may each be operated, owned, and/or otherwise controlled by the same entity or different entities. In some embodiments, one or more of the order processing stations 102 are separately owned and operated. In other embodiments, one or more of the order processing stations 102 and the fulfillment gateway 106 are owned by separate entities. In this case, the owner of the order processing station 102 may contract with the owner of the fulfillment gateway 106 for its services.

The fulfillment gateway 106 may be in a client-server relationship with the order processing stations 102 and/or the order fulfillment stations 108, a peer-to-peer relationship with the order processing stations 102 and/or the order fulfillment stations 108, or in a different type of relationship with the order processing stations 102 and/or the order fulfillment stations 108.

The order processing stations 102, the order fulfillment stations 108 and the fulfillment gateway 106 may be in communication directly (e.g., through local storage) and/or through the network 104 (e.g., in a cloud configuration or software as a service) with a database 112. The database 112 may store patient data 114, client data 116, pharmacy data 118, order data 120 and/or activity data 122.

The patient data 114 includes information regarding the patients associated with prescriptions received by the order processing stations 102. Examples of patient data 114 include name, address, telephone number, e-mail address, prescription drug history, and the like. In some embodiments when the patient is a member of a prescription drug plan, the patient data 114 includes member data of the member. The patient data 114 may include a client identifier that identifies the client associated with the patient and/or a patient identifier that identifies the patient to the client. The patient data 114 may also include, by way of example, dispensation preferences such as type of label, type of cap, message preferences, language preferences, or the like. The patient data 114 may be accessed by the order processing station 102 and sent as prescription parameters with a prescription order to the fulfillment gateway 106. The patient data 114 may be accessed by the fulfillment gateway 106 to obtain the dispensation preferences.

The client data 116 includes information regarding the prescription drug network of the patient. Examples of the client data 116 include client identification number, company name, company address, contact name, contact telephone number, contact e-mail address, and fulfillment priority information. The fulfillment gateway 106 may access the client data 116 to obtain dispensation preferences, such as fulfillment priority information.

The pharmacy data 118 includes information regarding the order fulfillment stations 108. The pharmacy data 118 may include, by way of example, location data regarding the location of the order fulfillment stations 108, an order fulfillment station identification number, information data regarding availability (e.g., backlog, hours of operation) at the order fulfillment stations 108, inventory data regarding inventory of prescription drugs at the order fulfillment stations 108, and specialization data regarding any prescription fulfillment processes in which the order fulfillment stations 108 specialize. The pharmacy data 118 may also include cost-to-fill values for prescribed drugs filled for each of the order fulfillment stations 108. The pharmacy data 118 may include dispensary attributes. Dispensary attributes may include capabilities and characteristics of the order fulfillment station 108, such as marking caps or vials, specialty packaging, cold rooms, added security for class C-2 narcotic prescription drugs, or the like.

The order data 120 may include data used for completion of the prescription, such as prescription materials. Prescription materials are a type of order materials that include an electronic copy of information regarding the prescription drug for inclusion with the fulfilled prescription. The prescription materials may include electronic information regarding drug interaction warnings, recommended usage, possible side effects, etc.

The activity data 122 may include data regarding the historic activity of the fulfillment gateway 106 for access when the fulfillment of the prescription is desired to be stopped or cancelled, as described below. The activity data 122 may include data relating to the order fulfillment by the order fulfillment station 108.

Figure 2:
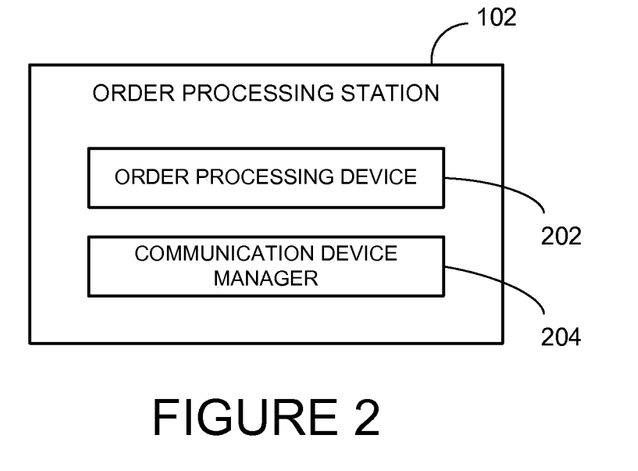
FIG. 2 is a block diagram of an order processing station that may be deployed within the system of FIG. 1, according to an example embodiment.

FIG. 2 illustrates the order processing station 102, according to an example embodiment. The order processing station 102 of FIG. 2 may be deployed in the system 100 as one or more of the order processing stations 102(a)-(n), or may otherwise be used.

The order processing station 102 of FIG. 2 includes an order processing device 202 and a communication device manager 204. Prescription data associated with a prescription is input into the order processing device 202 to create a prescription order. In general, a prescription order is an electronic record of the original prescription containing a prescription parameter. A single prescription parameter or multiple prescription parameters may be included. The electronic record may be stored in various memory devices and accessed electronically. The prescription may be entered into the order processing device 202 manually, such as when a paper prescription is inputted, or may be transcribed such as when a voicemail or phone call from a prescriber is inputted.

A communications manager 204 of the order processing station 102 obtains the prescription order from the order processing device 202 and sends the prescription order to the fulfillment gateway 106 via the network 104.

Figure 3:
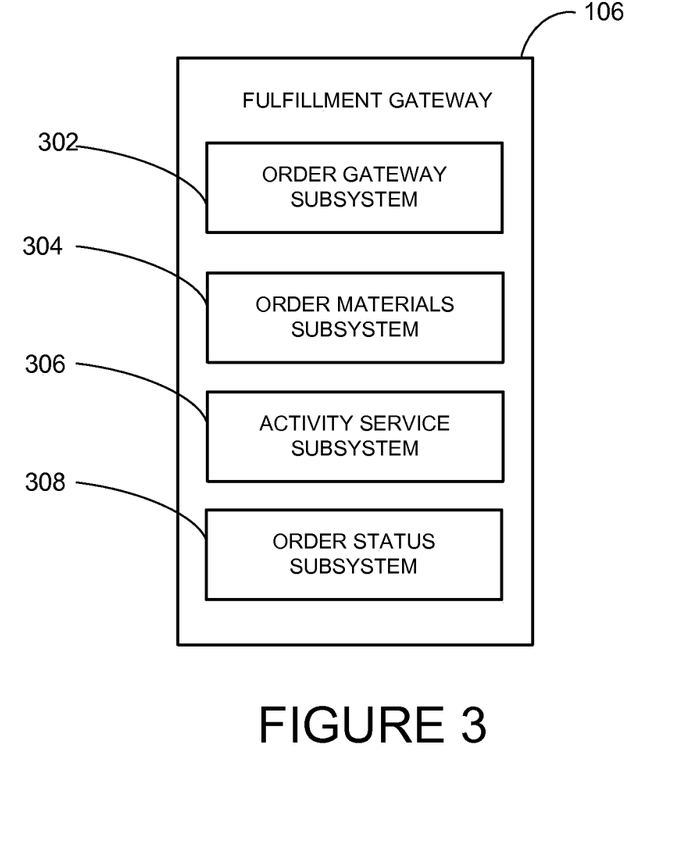
FIG. 3 is a block diagram of an example fulfillment gateway that may be deployed within the system of FIG. 1, according to an example embodiment.

FIG. 3 illustrates the fulfillment gateway 106, according to an example embodiment. The fulfillment gateway 106 may be deployed in the system 100, or may otherwise be used.

The fulfillment gateway 106 receives prescription orders and associates the prescription orders with an order message containing information for the order fulfillment stations 108 to fulfill the prescription according to the prescription order. The fulfillment gateway 106 may include an order gateway subsystem 302, an order materials subsystem 304, an activity service subsystem 306, and/or an order status subsystem 308. Other subsystems may also be included.

The order gateway subsystem 302 manages communications for the fulfillment gateway 106, including coordination of communications to/from the order material subsystem 304, the activity service subsystem 306, and an order status subsystem 308. The order gateway subsystem 302 provides communications for receiving prescription orders from the order processing station 102. The order gateway subsystem 302 may also provide a storage unit for order messages that are assigned or not yet assigned to various order fulfillment stations 108, as described in more detail below.

The order materials subsystem 304 obtains order materials for use at the order fulfillment station 108. The order materials are an electronic record of information needed by the order fulfillment station 108 to implement fulfillment of the prescription according to policies and preferences of patients, clients and the order fulfillment station 108. Thus, an electronic record is developed for the order fulfillment station 108 at the fulfillment gateway 106, thereby limiting the order fulfillment station's 108 reliance on the order processing station 102 for information. In some embodiments, order materials are stored at the fulfillment gateway 106, while in other embodiments the order materials are obtained from the order processing station 102. In other embodiments, order materials are aggregated from the order data 120 by accessing the database 112. The order materials are included in the order message associated with the prescription order. Order materials may include at least some portions of the patient data 114, the client data 116, the pharmacy data 118, prescription parameters, dispensation preferences and/or prescription materials.

Prescription materials are a type of order materials that include information regarding the prescription drug for inclusion with the fulfilled prescription. The prescription materials may include electronic information regarding drug interaction warnings, recommended usage, possible side effects, etc. for printing at the order fulfillment station 108 and inclusion with the fulfilled prescription for shipping. The order materials subsystem 304 may electronically format the order materials into fields useable at the order fulfillment station 108. For example, the patient data 114 and/or or the client data 116 may include dispensation preferences such as the inclusion of an invoice with the fulfilled prescription, the inclusion of a return envelope for remitting payment with the fulfilled prescription, the use of a child proof cap, the inclusion of reminders printed on a label, cap or leaflet, the inclusion of consumer survey leaflets, the inclusion of a message encouraging therapy adherence on a label, cap or leaflet, or the like.

The activity service subsystem 306 tracks operations performed by the fulfillment gateway 106 and stores the operations for historical reporting and visibility in the activity data 122, for example.

In some embodiments, through the order gateway 302, the order status subsystem 308 receives order status updates from the order fulfillment station 108 periodically. The order status subsystem 308 keeps an update on a prescription order as it progresses through the order fulfillment station 108 and/or fulfillment gateway 106 for possible intervention in the fulfillment. The order status subsystem 308 has the capability of instructing that a prescription order be cancelled, paused, or changed. Cancelling, pausing, or changing the prescription order may avoid the fulfillment of prescriptions that are no longer needed by the patient and are therefore of little use. For example, if a patient decides to transfer the prescription to another pharmacy, the order status subsystem 308 determines the status of the order and sends a command to cancel the prescription order via the order gateway 302 to the order fulfillment station 108. An example of changing the prescription order may be the substitution of a drug in the same class with the previously prescribed drug because of recent formulary changes. Changing the prescription order may include changing prescription parameters such as the address of the patient.

Figure 4:
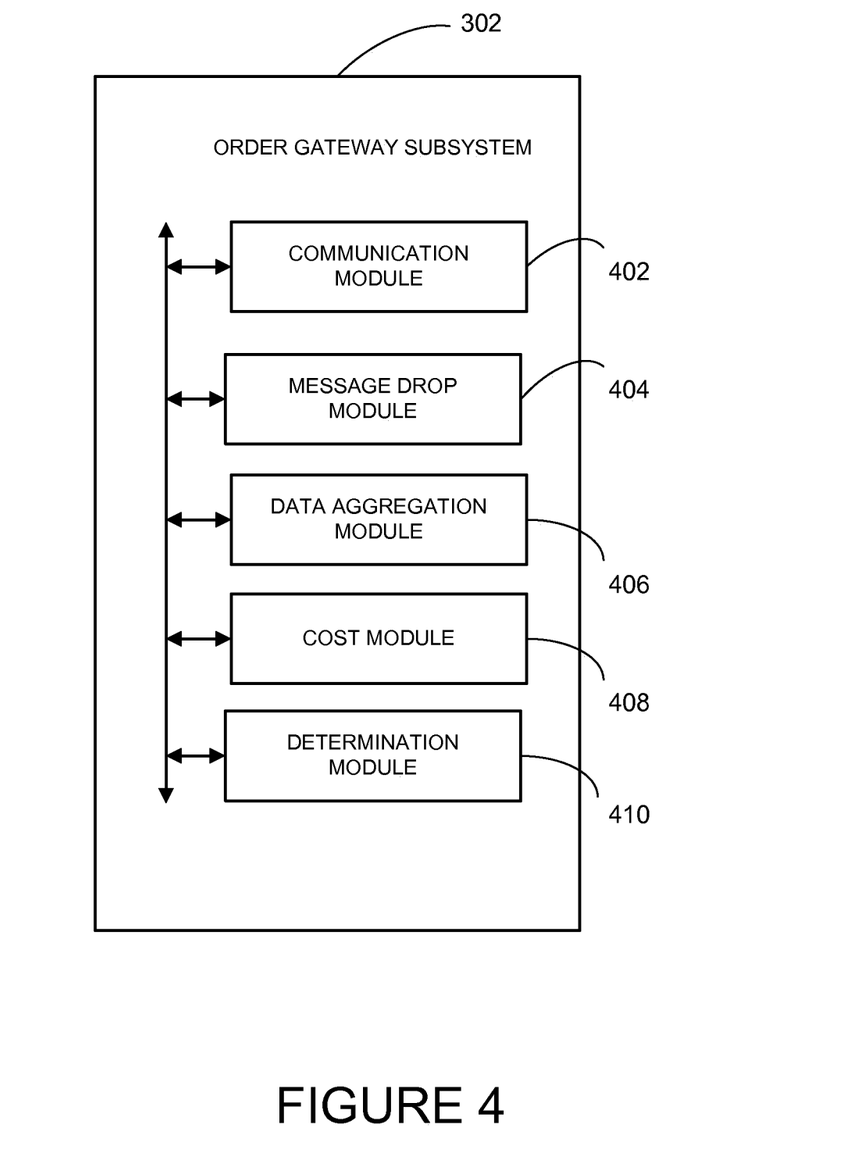
FIG. 4 is a block diagram of an example order gateway subsystem that may be deployed within the fulfillment gateway of FIG. 3, according to an example embodiment.

FIG. 4 illustrates the order gateway subsystem 302, according to an example embodiment. The order gateway subsystem 302 may be deployed in the fulfillment gateway 106, or may otherwise be used.

One or more modules are communicatively coupled and included in the order gateway subsystem 302 to enable communication with the order processing stations 102 and the order fulfillment stations 108. The order gateway subsystem 302 may include a communication module 402, a message drop module 404, a data aggregation module 406, a cost module 408 and a determination module 410. In one embodiment, the modules are deployed in memory and executed by a processor coupled to the memory. The functionality contained within the modules 402-410 may be combined into a lesser number of modules, further divided among a greater number of modules, or redistributed among existing modules. Other configurations including the functionality of the modules 402-410 may be used.

The communication module 402 communicatively links the fulfillment gateway 106 to the network 104. The communication module 402 handles transmission and receipt of data between two or more data sources using one or more communication protocols such as machine to machine communications and machine to enterprise communications.

The message drop module 404 provides storage containment of assigned order messages until they are pulled or downloaded by the order fulfillment station 108. For example, the message drop module 404 utilizes post office protocol (POP) or internet message access protocol (IMAP) for retrieval of the order messages by the order fulfillment station 108. The order fulfillment station 108 may access the message drop module 404 to pull (e.g. download) the order messages assigned to it at a desired frequency to obtain more prescription orders. In some embodiments, the order gateway subsystem 302 (see FIG. 3) may access the message drop module 404 and push (e.g. send) the message order to the order fulfillment station 108. Furthermore, the order status subsystem 308 (see FIG. 3) may also access the message drop module 404 to change prescription parameters or dispensation preferences in the order message. The order status subsystem 308 may also pause or hold the order message in the message drop module 404, or may cancel or delete the order message in the message drop module 404.

In an example embodiment, the order gateway subsystem 302 contains order messages that are not assigned to a particular order fulfillment station 108. The order messages are stored in the message drop module 404 and analyzed by the determination module 410, as explained below.

The order gateway subsystem 302 may include a data aggregation module 406 for aggregating data that includes prescription parameters, dispensation preferences and dispensary attributes. The data aggregation module 406 may obtain the prescription parameters, dispensation preferences and dispensary attributes from the order processing station 102, the order fulfillment station 108, the benefits manager device 110 and/or from the patient data 114, the client data 116 and/or the pharmacy data 118 in the database 112. Dispensation preferences may include implementation of corporate policies, such as inclusion of an envelope for remittance if not enrolled in automatic payment, printing of adherence messages and refill reminders. Dispensation preferences may include one or more patient preferences and/or one or more client preferences. Patient preferences that are relevant to the order fulfillment station 108 during fulfillment of the prescription order may include email notifications, specialty caps on vials, personalized refill reminder messages, personalized adherence messages, or the like.

Client preferences that are relevant to the order fulfillment station 108 may include specified shipping containers, mail carriers, specialty labels, brail printing capability, etc. Client preferences may also include the requirement that the prescription be fulfilled at the order fulfillment station 108 that allows unions or utilizes only union mail carriers. Client preferences also include client prioritization. That is, prescription orders from patients of certain clients may have a higher priority for fulfillment than other prescription orders. In other words, an age of the order message may be considered by the fulfillment gateway 106 when determining order fulfillment. The age of the order message is determined by the time of generation of the order message where the order message has not been delivered yet. Dispensary attributes are operational characteristics of the order fulfillment stations 108 served by the fulfillment gateway 106. Examples of dispensary attributes may include: for each order fulfillment station 108, inventory level or availability of prescription drugs; fulfillment of specialty drugs (e.g., compounding); inventory level or availability of specialty containers or caps; marking capability of labels, containers or caps; cost based calculations for the prescribed drugs capable of being fulfilled at the order fulfillment station 108; specialty packaging capability; operational cold rooms; added security for class C-2 narcotic prescription drugs; union-only labor; or the like.

The order gateway subsystem 302 may also include a cost module 408 to calculate cost based calculations for the order fulfillment station 108. The data aggregation module 406 and the cost module 408 may be communicatively coupled and included in the order gateway subsystem 302 to enable site selection. The cost based calculations include a calculated cost-to-fill value associated with each prescription drug at each of the order fulfillment stations 108 that the fulfillment gateway 106 serves. The cost-to-fill value may be stored as a portion of the pharmacy data 118 and updated by the cost module 408. The cost-to-fill value may be the cost to fulfill a prescribed drug based on costs of labor, shipping, and/or materials, for example, at the order fulfillment station 108. Cost for labor, shipping, and materials may be weighted as desired. Cost of materials may include cost of prescription drugs purchased from distributors, as well as prescription drug containers, caps, packaging supplies, or the like. The cost-to-fill value of the prescription drug may vary among order fulfillment stations 108, (e.g., each order fulfillment station 108 having its own, but not necessarily unique, cost-to-fill value per prescription drug). For example, if one of the order fulfillment stations 108 is highly automated, it may have a lower cost-to-fill value than another of the order fulfillment stations 108. More specifically, if the order fulfillment station 108 has in place an automated process to fulfill a type of prescribed drug but another order fulfillment station 108 requires manual fulfillment, the cost-to-fill may be lower for automated fulfillment.

The cost based calculations, calculated by the cost module 408, may include a maximum variance value for prescription drugs fulfilled by the order fulfillment stations 108. In some embodiments, the maximum variance may be preset and stored in memory. In general, the maximum variance value is a maximum variance in the cost-to-fill value that is tolerable to ensure efficient fulfillment of the prescription order. Fulfillment of the prescription order at an order fulfillment station 108 having a cost-to-fill value greater than the lowest cost-to-fill value among multiple order fulfillment stations 108 may be acceptable in some circumstances where the maximum variance value is not exceeded. The maximum variance value is exceeded when the cost-to-fill value of the order fulfillment station 108 is greater than a reference cost-to-fill value (e.g. lowest cost-to-fill value among multiple order fulfillment stations 108). An example of a circumstance in which the maximum variance is considered is the case of a backlog at one of the order fulfillment stations 108. Another example is when client priority, i.e., age of the order message, causes the selection of an order fulfillment station 108 with a higher cost-to-fill value (that does not exceed the reference cost-to-fill value by the maximum variance value) to ensure timely fulfillment.

The order gateway subsystem 302 may include a determination module 410 that may communicate with the data aggregation module 406 and the cost module 408. The determination module 410 utilizes a rule-based site selection process based on prioritization of the prescription parameters, the dispensation preferences, and the dispensary attributes to determine the appropriate order fulfillment station 108 to send the order message. The determination module 410 may update its determination upon a sudden price increase in the prescription drug, a reduction in backlog, a change in formulary, or the like. In such a case, the determination module 410 may access the message drop module 404 to update or refresh the selection among order fulfillment stations 108. The determination module 410 may access the message drop module 404 in the event that the order message needs to be reassigned to a different order fulfillment station 108. That is, the determination module 410 may readdress the order message before it is downloaded by the originally assigned order fulfillment station 108.

The determination module 410 may accumulate multiple order messages into a batch for delivery to the order fulfillment station 108. The order fulfillment station 108 may request a specific number of order messages in the batch. That is, the order fulfillment station 108 may identify a desired number of order messages in the batch for delivery. In response, the determination module 410 may accumulate no more order messages than the identified desired number.

In the embodiment in which the order messages are stored in the message drop module 404 without assignment to a particular order fulfillment station 108, the determination module 410 may determine which order messages are appropriate for delivery to the order fulfillment station 108. The determination may be based on dispensary attributes, such as cost-to-fill values, and dispensation preferences, such as maximum variance values. In response to the order fulfillment station 108 requesting a batch of multiple order messages from the fulfillment gateway 106, the determination module may 410 determine which order messages have the lowest cost-to-fill values. For example, the dispensary attribute of an order fulfillment station 108 may include a cost-to-fill value for Fluoxetine 60 mg that is the lowest of all of the multiple order fulfillment stations 108. In this case, order messages associated with prescription orders for Fluoxetine 60 mg are delivered from the message drop module 404 to the order fulfillment station 108 with the lowest cost-to fill value.

Regardless of whether the order messages are stored in the message drop module 404 as assigned or unassigned, the order messages may be delivered to the order fulfillment station 108 by pushing or pulling. The order fulfillment station 108 may access the message drop module 404 to pull (e.g. download) the order messages assigned to it at a desired frequency to obtain more prescription orders. In some embodiments, the order gateway subsystem 302 (see FIG. 3) may access the message drop module 404 and push (e.g. send) the order message to the order fulfillment station 108.

Furthermore, the order fulfillment station 108 may request order messages or the fulfillment gateway 106 may send the order messages without a request. Examples of sending the order message without a request may include sending a high priority order message to the order fulfillment station 108 or sending the order message at a preset frequency.

In an example embodiment, the order fulfillment station 108 that takes delivery of the order messages is an under capacity order fulfillment station 108. Under capacity, as used herein, is intended to impart the real-time existence of a less than desired workload or anticipation of a less than desired work load.

The determination module 410 may select order messages based on dispensation preferences, such as maximum variance. Specifically, upon receiving a request for a batch of order messages from the fulfillment gateway 106, the determination module 410 may compare the cost-to-fill value for the prescription drug at the requesting order fulfillment station 108 with the maximum variance for the prescription drug. If the cost-to-fill value of the requesting order fulfillment station 108 does not exceed the lowest cost-to-fill value (attributed to another order fulfillment station 108) by the maximum variance value, the order message for the prescription drug is provided to the requesting order fulfillment station 108.

The cost module 408 and/or the determination module 410 may adjust the maximum variance value based on dispensation preferences, such as age of order or client priority, or based on dispensary attributes, such as the loss or substantial incapacitation of an order fulfillment station 108.

Furthermore, the determination module 410 may determine age of the order message based on the time of generating the order message. That is, the order has been generated by the fulfillment gateway 106 but not yet delivered. The time of generating the order message may be a prescription parameter of the order message. The determination module 410 may access dispensation preferences, stored locally or at the database 112, and compare the age of the message order with the dispensation preference. In an example embodiment, the dispensation preference may include an age threshold. The age threshold is a threshold that limits the order message's time in storage at the message drop module 404. If the determination module 410 determines that the order message has aged, starting from the time of generating, past the age threshold, the determination module 410 may communicate with the communication module 402. The communication module 402 may send the order message to an order fulfillment station 108 to begin fulfillment. The determination module 410 may also select order messages for delivery to the order fulfillment station 108 based on age without consideration of age threshold. For example, older order messages are selected before new order messages.

Figure 5:
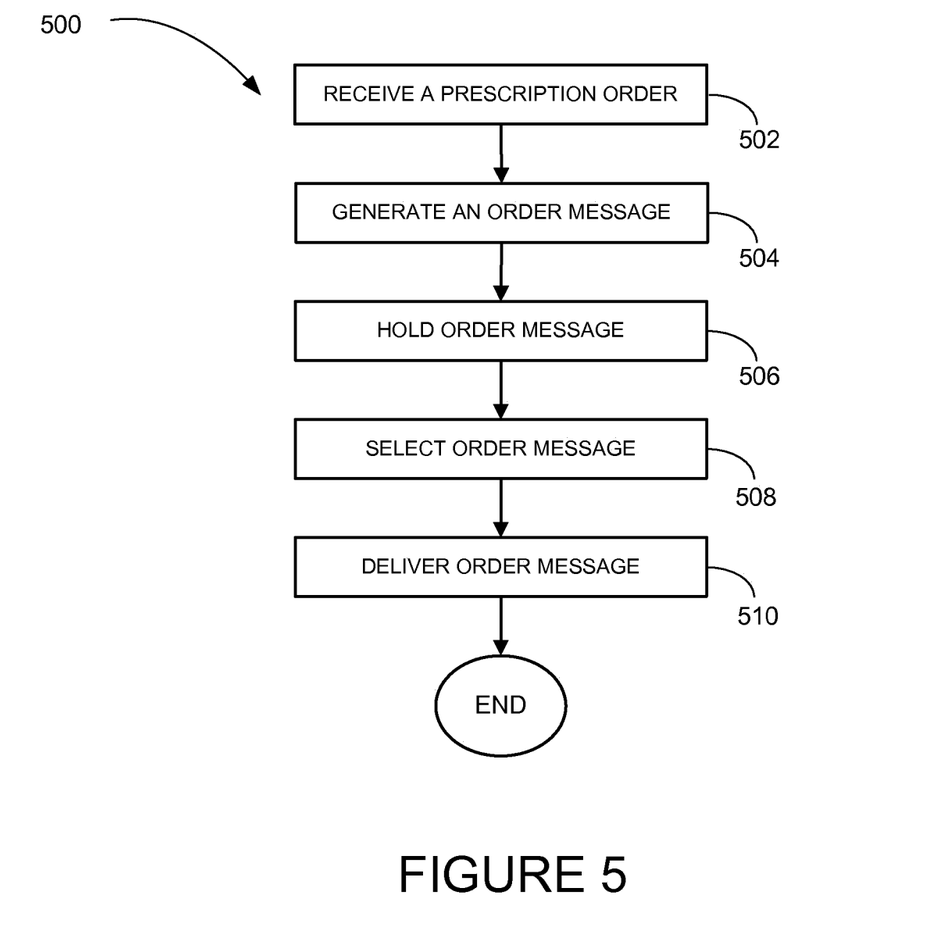
FIG. 5 is an example process flow illustrating a method for fulfillment, according to an example embodiment.

Referring now to FIG. 5, a method 500 for fulfillment according to an example embodiment is illustrated. The method 500 may be performed by the fulfillment gateway 106, partially by the order processing station 102, partially by the order fulfillment station 108, partially by other stations for fulfillment or may otherwise be performed.

A patient or prescriber submits a prescription for one or more prescription drugs to an order processing station 102 for fulfillment. After verification of the prescription, the order processing station 102 creates an electronic record of the prescription and sends the same to the fulfillment gateway 106 as a prescription order with one or more prescription parameters. At block 502, the fulfillment gateway 106 receives the prescription order for the one or more prescription drugs from the order processing station 102.

The fulfillment gateway 106 generates an order message associated with the prescription order at block 504. The fulfillment gateway 106 may communicate with the order processing station 102, the benefit manager device 110 and/or the database 112 over the network 104 to obtain or otherwise access one or more prescription parameters and/or one or more dispensation preferences for writing to the order message. By including the prescription parameters and/or dispensation preferences in the order message, the fulfillment gateway 106 provides electronic information for the order fulfillment station 108 to fulfill the prescription. In some embodiments, the order message contains all or substantially all of the information needed by the order fulfillment station 108 to fulfill the prescription.

At block 506, the order message is held at the message drop module 404. In some embodiments, the order message is not assigned to an order fulfillment station 108. While being held, the determination module 410 may update or refresh prescription parameters and/or dispensation preferences of the order message.

Selection of the order message from the message drop module 404 at block 508 is based on the prescription parameter, the dispensation preference, and/or the dispensary attribute. In some embodiments, selection is not based on assignment. That is, the order messages are not assigned before selection. The fulfillment gateway 106 may communicate with the order fulfillment station 108 and/or the database 112 over the network 104 to obtain the one or more dispensary attributes.

The selected order message is delivered to the order fulfillment station 108 at block 510. Delivery may include the order message being pulled by the order fulfillment station 108 or pushed by the fulfillment gateway 106.

Figure 6:
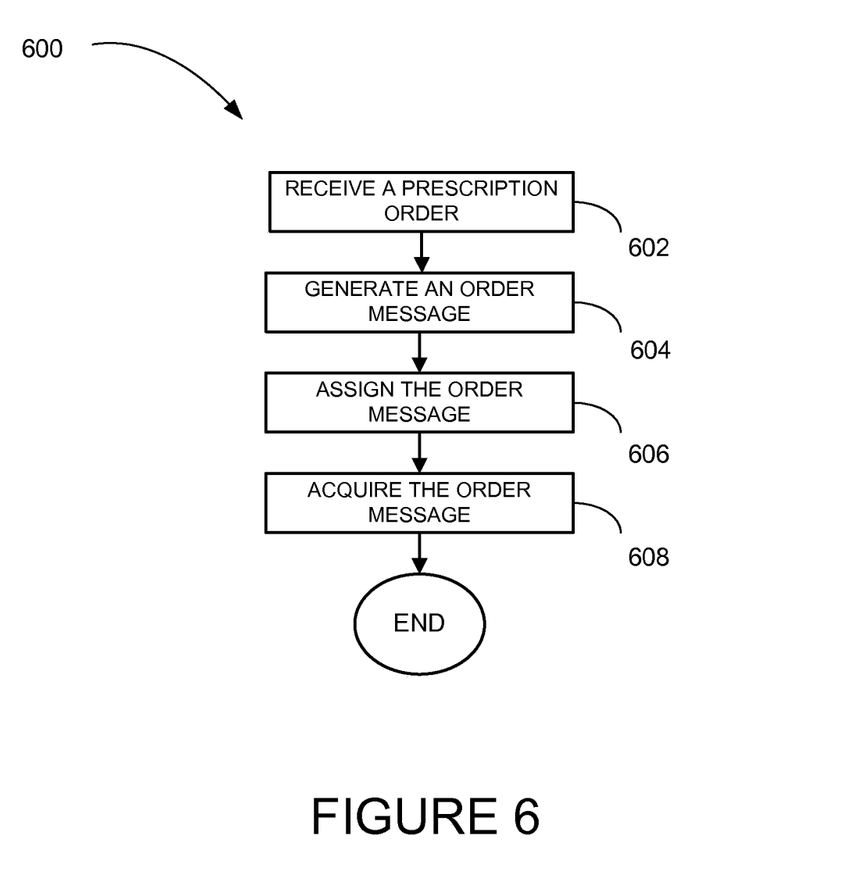
FIG. 6 is an example process flow illustrating a method for fulfillment, according to an example embodiment.

Referring now to FIG. 6, a method 600 for fulfillment according to an example embodiment is illustrated. The method 600 may be performed by the fulfillment gateway 106, partially by the order processing station 102, partially by the order fulfillment station 108, or partially by other stations for fulfillment or may otherwise be performed.

A patient or prescriber submits a prescription for one or more prescription drugs to an order processing station 102 for fulfillment. After verification of the prescription, the order processing station 102 creates an electronic record of the prescription and sends the same to the fulfillment gateway 106 as a prescription order with one or more prescription parameters. At block 602, the fulfillment gateway 106 receives the prescription order for the one or more prescription drugs from the order processing station 102.

The fulfillment gateway 106 generates an order message associated with the prescription order at block 604. The fulfillment gateway 106 may communicate with the order processing station 102, the benefit manager device 110 and/or the database 112 over the network 104 to obtain or otherwise access one or more prescription parameters and/or one or more dispensation preferences for writing to the order message. By including the prescription parameters and/or dispensation preferences in the order message, the fulfillment gateway 106 provides electronic information for the order fulfillment station 108 to fulfill the prescription. In some embodiments, the order message contains all or substantially all of the information needed by the order fulfillment station 108 to fulfill the prescription.

Assignment of the order message at block 606 is based on one or more prescription parameters, one or more dispensation preferences, and/or one or more dispensary attributes.

The fulfillment gateway 106 may communicate with the order fulfillment station 108 and/or the database 112 over the network 104 to obtain the one or more dispensary attributes.

The assigned order fulfillment station 108 acquires the order message at block 608 by pulling or downloading the order message. Utilizing the information in the order message, including the one or more prescription parameters, the one or more dispensation preferences, and/or the one or more dispensary attributes, the order fulfillment station 108 fulfills the prescription according to the prescription order.

Figure 7:
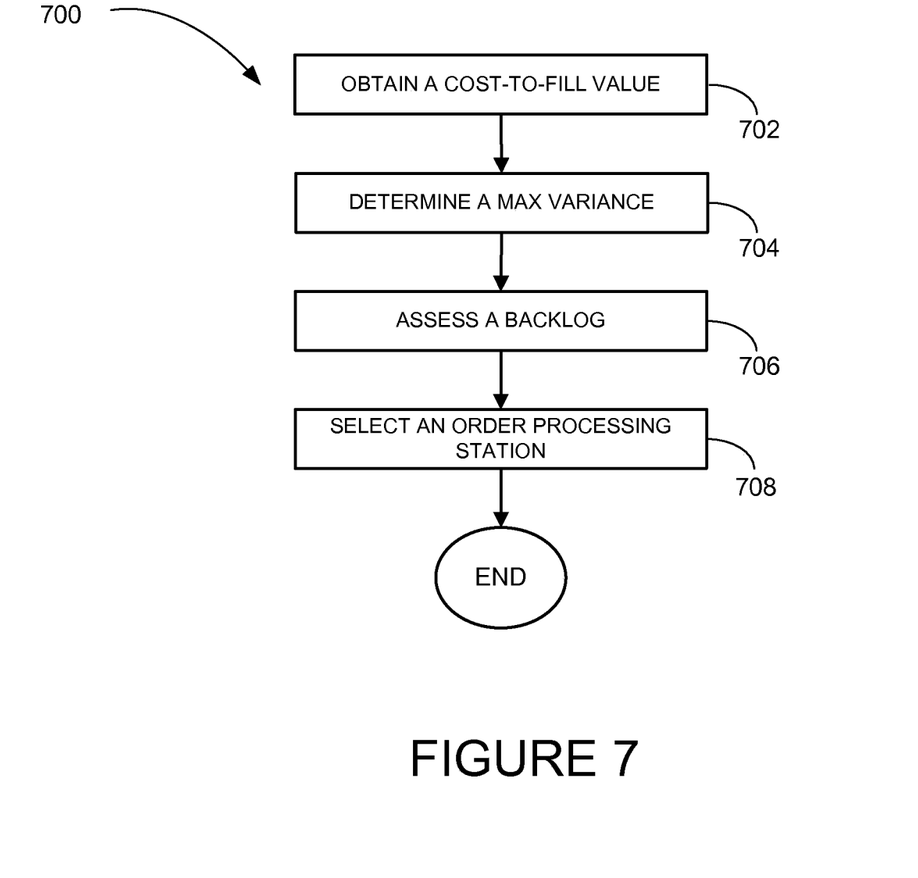
FIG. 7 is an example process flow illustrating a method for fulfillment, according to an example embodiment.

FIG. 7 illustrates a method 700 for fulfillment according to an example embodiment. The method 700 may be performed by the fulfillment gateway 106 or may otherwise be performed.

The fulfillment gateway 106 prioritizes fulfillment by considering cost based calculations. In the example method 700 of FIG. 7, at block 702, the fulfillment gateway 106 may access a cost-to-fill value for a prescription to be fulfilled at one of the order fulfillment stations 108. The cost-to-fill value may be calculated at the fulfillment gateway 106, received through the network 104 from other data sources, or obtained from memory in the fulfillment gateway 106.

At block 704, a maximum variance value for a prescription drug is determined. The fulfillment gateway 106 assesses a backlog of prescription orders at the order fulfillment stations 108 at block 706. The backlog may be determined by the number of addressed order messages in the message drop 404 or by the number of downloads from the order fulfillment station 108, for example. If no backlog, or if the backlog is such that it will not cause the age of the prescription order to exceed client priority preferences, the fulfillment gateway 106 selects an order fulfillment station 108 for fulfillment based on the lowest cost-to-fill value at block 708. For some prescription orders, the fulfillment gateway 106 may determine that the order fulfillment station 108 with the lowest cost-to-fill value has a backlog that would cause the age of the prescription order to become unacceptable. In such a case, the fulfillment gateway 106 selects an order fulfillment station 108 with an associated cost-to-fill value for the prescription drug that exceeds the lowest cost-to-fill value by no more than the maximum variance value at block 708.

Figure 8:
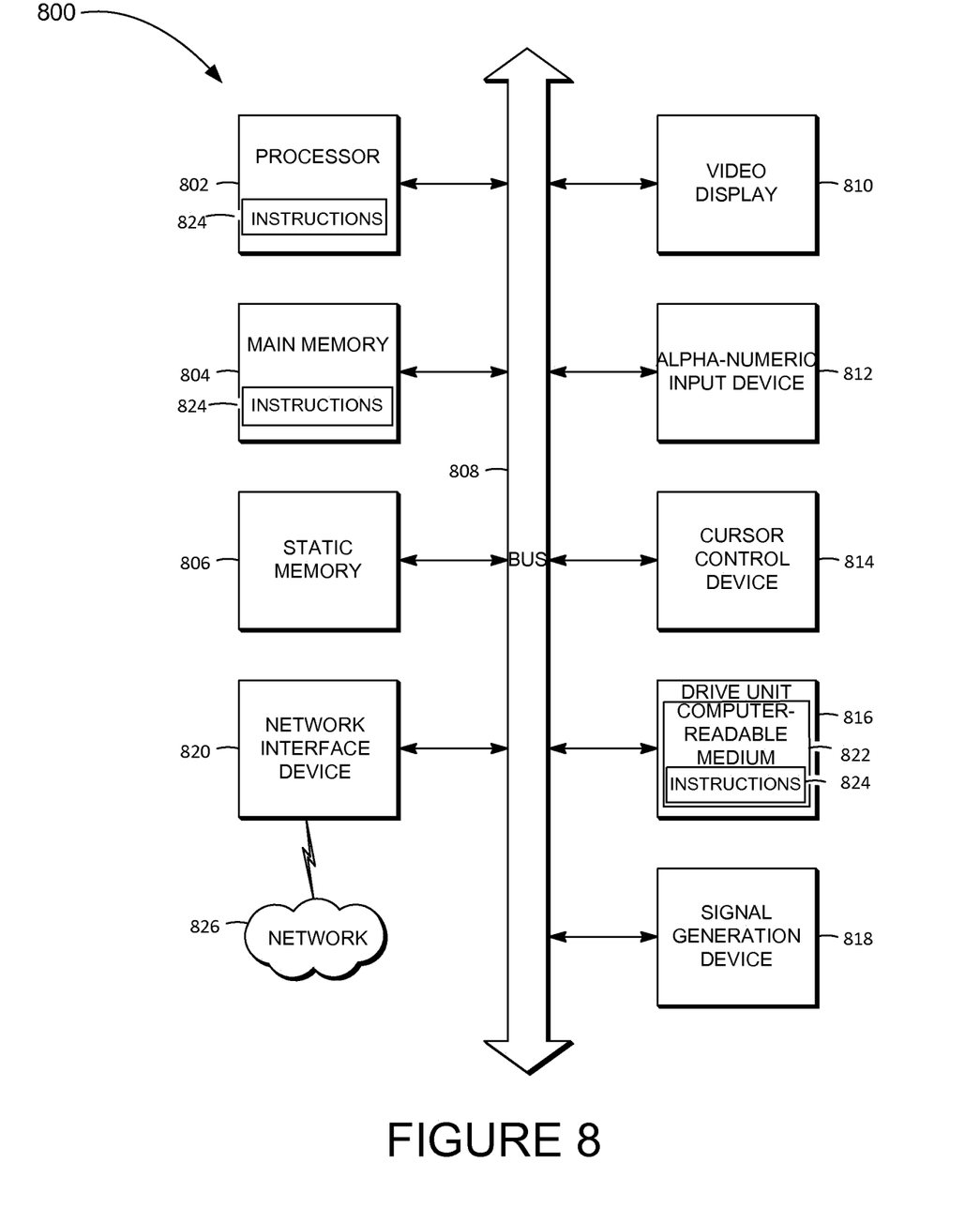
FIG. 8 is a block diagram of a machine in the example form of a computer system within which a set of instructions for causing the machine to perform any one or more of the methodologies discussed herein may be executed or stored.

FIG. 8 shows a block diagram of a machine in the example form of a computer system 800 within which a set of instructions may be executed causing the machine to perform any one or more of the methods, processes, operations, or methodologies discussed herein. The order processing station 102, the fulfillment gateway 106, the order fulfillment station 108, the benefit manager device 110 and/or the database 112 may include the functionality of the one or more computer systems 800.

In an example embodiment, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a server computer, a client computer, a personal computer (PC), a tablet PC, a gaming device, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 800 includes a processor 802 (e.g., a central processing unit (CPU) a graphics processing unit (GPU) or both), a main memory 804 and a static memory 806, which communicate with each other via a bus 808. The computer system 800 further includes a video display unit 810 (e.g., a liquid crystal display (LCD) or a cathode ray tube (CRT)). The computer system 800 also includes an alphanumeric input device 812 (e.g., a keyboard), a cursor control device 814 (e.g., a mouse), a drive unit 816, a signal generation device 818 (e.g., a speaker) and a network interface device 820.

The drive unit 816 includes a computer-readable medium 822 on which is stored one or more sets of instructions (e.g., software 824) embodying any one or more of the methodologies or functions described herein. The software 824 may also reside, completely or at least partially, within the main memory 804 and/or within the processor 802 during execution thereof by the computer system 800, the main memory 804 and the processor 802 also constituting computer-readable media.

The software 824 may further be transmitted or received over a network 826 via the network interface device 820. The network 826 may represent the network 104 of FIG. 1.

While the computer-readable medium 822 is shown in an example embodiment to be a single medium, the term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing or encoding a set of instructions for execution by the machine and that cause the machine to perform any one or more of the methodologies of the present invention. The term "computer-readable medium" shall accordingly be taken to include, but not be limited to, solid-state memories, optical media, and magnetic media. In some embodiments, the computer-readable medium is a non-transitory computer-readable medium.

The term "based on" or using, as used herein, reflects an open-ended term that can reflect others elements beyond those explicitly recited.

Certain systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled.

The inventive subject matter may be represented in a variety of different embodiments of which there are many possible permutations.

In an example embodiment, a prescription order for a prescription drug is received. An order message associated with the prescription order is generated at a fulfillment gateway. The order message has a prescription parameter and a dispensation preference for fulfilling the prescription order. The prescription parameter and the dispensation preference provide information for fulfilling the prescription order. The fulfilling includes dispensing the prescription drug. The order message for delivery is held. The order message is selected for delivery based on the prescription parameter, the dispensation preference and a dispensary attribute of an order fulfillment station.

In an example embodiment, a prescription order for a prescription drug is received from an order processing station. An order message associated with the prescription order is generated. The order message has a prescription parameter and a dispensation preference for fulfilling the prescription order. The prescription parameter and the dispensation preference provide information for fulfilling the prescription order. The fulfilling includes dispensing the prescription drug. The order message is assigned to an order fulfillment station based on the prescription parameter, the dispensation preference and a dispensary attribute of the order fulfillment station.

In an example embodiment, a cost-to-fill value for a prescription drug at a plurality of order fulfillment stations is obtained. The cost-to-fill value includes costs for one or more of shipping, labor and materials. A maximum variance value for the prescription drug is determined on a processor. The maximum variance value is a tolerable cost to ensure efficient fulfillment of the prescription drug. A backlog of prescription orders awaiting fulfillment at a first order fulfillment station of the plurality of order fulfillment stations is assessed. The first order fulfillment station has a lowest cost-to-fill value for the prescription drug. One of the plurality of order fulfillment stations for fulfillment of the prescription drug is selected based on the cost-to-fill value, the maximum variance value for the prescription drug, and assessment of the backlog of prescription orders.

While described herein as a prescription fulfillment system, examples of the present disclosure further include drug order. Examples of drug order fulfillment can include wholesale distribution of controlled drugs/controlled substances, which have specific controls imposed on distribution by a governmental entity. Specific examples may include order fulfillment of hemp plants for manufacturing processing, movement of controlled substances from manufacturer to a pharmacy, a second manufacturer, a laboratory, etc. Accordingly, the order processing station provides processing of an order for a controlled substance to develop a controlled substance order for sending to an order fulfillment station via a fulfillment gateway. When the controlled substance order arrives at the fulfillment gateway from the order processing station, an order fulfillment station has not been selected. The fulfillment gateway associates the controlled substance order with an order message and provides information needed for an order fulfillment station to fulfill the controlled substance according to the controlled substance order. The fulfillment gateway selects the order fulfillment station based on controlled substance parameters, dispensation preferences and dispensary attributes. Rules and/or priorities for treatment of various controlled substance parameters, dispensation preferences and dispensary attributes may govern selection of an order fulfillment station. The fulfillment gateway described herein is sensitive to cost of labor, material, and shipping involved with fulfillment of a controlled substance according to a controlled substance order. The fulfillment gateway holds completed controlled substance orders associated with order messages for the order fulfillment station to pull or download from the fulfillment gateway as needed. Furthermore, the fulfillment gateway may track progress of fulfillment at order fulfillment stations. Thus, the order fulfillment station does not have to request updates from the order processing station. Indeed, the order fulfillment station does not need to communicate with the order processing station. That is, the order fulfillment station is independent or decoupled from the order processing station. Thus, irrespective of the status of the order processing station, the fulfillment gateway allows routing and fulfillment to continue. The fulfillment gateway allows delay of a routing decision so that an order fulfillment station does not need to be selected at the order processing station. The fulfillment gateway provides capabilities for changing routing of the controlled substance order. That is, by tracking progress, the fulfillment gateway may stop, pause, cancel or change controlled substance orders during fulfillment of the controlled substance. The above description can be read to include controlled substance fulfillment as a further embodiment that can be executed using the methods and systems described herein.

Thus, methods and systems for fulfilling a prescription or drug order have been described. Although embodiments of the present invention have been described with reference to specific example embodiments, it will be evident that various modifications and changes may be made to these embodiments without departing from the broader spirit and scope of the embodiments of the invention. Accordingly, the specification and drawings are to be regarded in an illustrative rather than a restrictive sense.

The methods described herein do not have to be executed in the order described, or in any particular order. Moreover, various activities described with respect to the methods identified herein can be executed in serial or parallel fashion. Although "End" blocks are shown in the flowcharts, the methods may be performed continuously.

The Abstract of the Disclosure is provided to comply with 37 C.F.R. § 1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

What is claimed is:

1. A drug dispensing system comprising:
   a plurality of fulfillment stations, wherein each station of the plurality of fulfillment stations is:
      characterized by a respective set of dispensary attributes; and
      configured to, in response to receiving a first order message including a first unique drug identifier, fill a container with pills matching the first unique drug identifier;
   an order gateway subsystem including one or more processors that implement:
      a communication module configured to communicate with an order processing station over a digital communications network to obtain prescription orders from the order processing station;
      a message drop module configured to store a plurality of order messages corresponding respectively to the obtained prescription orders;
      a data aggregation module configured to obtain the sets of dispensary attributes for the plurality of fulfillment stations; and
      a routing determination module configured to, for each order message of the plurality of order messages:

select one of the plurality of fulfillment stations based on compatibility between dispensary attributes for the selected one of the plurality of fulfillment stations and dispensation preferences specified by the order message; and transmit the order message to the selected one of the plurality of fulfillment stations over the digital communications network; and an order status subsystem configured to conditionally send a cancellation instruction relating to one of the plurality of order messages to the respective selected one of the plurality of fulfillment stations over the digital communications network to cancel dispensing of pills based on an indication of order status for a respective prescription order associated with the one of the plurality of order messages, wherein each of the plurality of fulfillment stations is configured to, in response to receiving a first cancellation instruction indicating a specified order message, terminate dispensing of pills corresponding to the specified order message.

2. The drug dispensing system of claim 1 wherein:
the order status subsystem is configured to receive status updates from the plurality of fulfillment stations regarding transmitted order messages, and
the status updates include a corresponding indication of order status for at least one of the obtained prescription orders.

3. The drug dispensing system of claim 1 wherein the data aggregation module is configured to obtain dispensation preferences for an entity associated with the first order message.

4. The drug dispensing system of claim 1 wherein at least one station of the plurality of fulfillment stations includes a high-volume drug dispenser apparatus.

5. The drug dispensing system of claim 1 wherein the dispensary attributes for one of the plurality of fulfillment stations describe physical capabilities of the one of the plurality of fulfillment stations relating to filling containers with pills matching unique drug identifiers.

6. The drug dispensing system of claim 5 wherein the dispensary attributes include at least one of (i) an indication of availability of specialty packaging, (ii) an indication of availability of cold storage, (iii) an indication of availability of security facilities for controlled substances, (iv) an indication of ability to apply markings to containers, and (v) an indication of fulfillment station availability.

7. The drug dispensing system of claim 1 further comprising:
a fulfillment gateway comprising a memory and a processor coupled to the memory and configured to execute instructions from the memory,
wherein the fulfillment gateway includes the order gateway subsystem and the order status subsystem.

8. The drug dispensing system of claim 1 further comprising:
an order materials subsystem configured to store electronic information to be rendered into printed form along with prescription containers,
wherein the electronic information is included in at least some of the plurality of order messages for printing and inclusion with filled containers.

9. The drug dispensing system of claim 1 further comprising:
a cost module configured to, for each order message of the plurality of order messages, determine cost of fulfillment at each of the plurality of fulfillment stations,
wherein the routing determination module is configured to select from the plurality of fulfillment stations based at least in part on the determined costs of fulfillment.

10. The drug dispensing system of claim 9 wherein:
the cost module is configured to, for a given order message of the plurality of order messages, determine a maximum variance value; and
the routing determination module is configured to, for the given order message, exclude from selection any of the plurality of fulfillment stations having a determined cost of fulfillment greater than the maximum variance value.

11. The drug dispensing system of claim 9 wherein the cost module is configured to, for a given order message of the plurality of order messages and a given fulfillment station of the plurality of fulfillment stations, determine the cost of fulfillment based on (i) a cost of labor to fulfill the given order message at the given fulfillment station, (ii) a cost of shipping from the given fulfillment station, and (iii) a cost of materials for the given order message.

12. The drug dispensing system of claim 1 wherein:
a particular prescription order of the obtained prescription orders specifies pills of a particular type for a particular user; and
the message drop module stores a particular order message corresponding to the particular prescription order.

13. The drug dispensing system of claim 12 wherein the routing determination module is configured to selectively reassign the particular order message to a different one of the plurality of fulfillment stations.

14. The drug dispensing system of claim 12 wherein the order status subsystem is configured to transmit a change request for the particular order message in response to a formulary change for the particular type of pills specified by the particular prescription order.

15. The drug dispensing system of claim 12 wherein:
the routing determination module is configured to select a particular fulfillment station of the plurality of fulfillment stations for the particular order message based on compatibility between (i) dispensation preferences for an entity associated with the first order message and (ii) dispensary attributes for the particular fulfillment station; and
the communication module is configured to transmit the plurality of order messages to respective selected ones of the plurality of fulfillment stations, including transmitting the particular order message to the particular fulfillment station to instruct the particular fulfillment station to fill a particular container with pills of the particular type for delivery to the particular user.

16. The drug dispensing system of claim 15 wherein:
the particular order message is associated with a generation time;
the dispensation preferences of the particular order message specify an age threshold; and
the order gateway subsystem is configured to transmit the particular order message to the particular fulfillment station in response to a time elapsing since the generation time exceeding the age threshold.

17. The drug dispensing system of claim 15 wherein:
the dispensation preferences of the particular order message specify a client priority; and
the order gateway subsystem is configured to transmit the particular order message to the particular fulfillment station in response to the client priority having higher precedence than client priorities of others of the plurality of order messages in the message drop module.

18. The drug dispensing system of claim 1 wherein:
the message drop module is configured to store an associated order message creation time with each of the plurality of order messages; and
ones of the plurality of order messages are selected for transmission by the communication module according to their associated order message creation times.

19. A computer-implemented method of operating a drug dispensing system, the method being executed by one or more processors and comprising:
obtaining dispensary attributes for each of a plurality of fulfillment stations, wherein each station of the plurality of fulfillment stations is:
characterized by a respective set of dispensary attributes; and
configured to, in response to receiving a first order message including a first unique drug identifier, fill a container with pills matching the first unique drug identifier;
communicating with an order processing station over a digital communications network to obtain prescription orders from the order processing station;
storing a plurality of order messages corresponding respectively to the obtained prescription orders;
for each order message of the plurality of order messages, selecting one of the plurality of fulfillment stations based on compatibility between dispensary attributes for the selected one of the plurality of fulfillment stations and dispensation preferences specified by the order message;
transmitting the order message to the selected one of the plurality of fulfillment stations over the digital communications network; and
conditionally sending a cancellation instruction relating to one of the plurality of order messages to the respective selected one of the plurality of fulfillment stations over the digital communications network to cancel dispensing of pills based on an indication of order status for a respective prescription order associated with the one of the plurality of order messages,
wherein each of the plurality of fulfillment stations, in response to receiving a first cancellation instruction indicating a specified order message, terminates dispensing of pills corresponding to the specified order message.

20. A non-transitory computer-readable medium comprising instructions that, when executed by one or more processors, cause the one or more processors to perform operations including:
obtaining dispensary attributes for each of a plurality of fulfillment stations, wherein each station of the plurality of fulfillment stations is:
characterized by a respective set of dispensary attributes; and
configured to, in response to receiving a first order message including a first unique drug identifier, fill a container with pills matching the first unique drug identifier;
communicating with an order processing station over a digital communications network to obtain prescription orders from the order processing station;
storing a plurality of order messages corresponding respectively to the obtained prescription orders;
for each order message of the plurality of order messages, selecting one of the plurality of fulfillment stations based on compatibility between dispensary attributes for the selected one of the plurality of fulfillment stations and dispensation preferences specified by the order message;
transmitting the order message to the selected one of the plurality of fulfillment stations over the digital communications network; and
conditionally sending a cancellation instruction relating to one of the plurality of order messages to the respective selected one of the plurality of fulfillment stations over the digital communications network to cancel dispensing of pills based on an indication of order status for a respective prescription order associated with the one of the plurality of order messages,
wherein each of the plurality of fulfillment stations, in response to receiving a first cancellation instruction indicating a specified order message, terminates dispensing of pills corresponding to the specified order message.

* * * * *